US010576302B2

(12) United States Patent
Grodzki et al.

(10) Patent No.: US 10,576,302 B2
(45) Date of Patent: Mar. 3, 2020

(54) METHOD AND APPARATUS FOR MONITORING A RADIATION THERAPY OF A PATIENT

(71) Applicant: Siemens Aktiengesellschaft, Munich (DE)

(72) Inventors: David Grodzki, Erlangen (DE); Annemarie Hausotte, Erlangen (DE); Bjoern Heismann, Erlangen (DE); Arne Hengerer, Moehrendorf (DE); Mark-Aleksi Keller-Reichenbecher, Sandhausen (DE); Sebastian Schmidt, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1350 days.

(21) Appl. No.: 14/838,566

(22) Filed: Aug. 28, 2015

(65) Prior Publication Data

US 2016/0059041 A1 Mar. 3, 2016

(30) Foreign Application Priority Data

Aug. 29, 2014 (DE) .................. 10 2014 217 283

(51) Int. Cl.
*A61N 5/10* (2006.01)
*A61B 5/055* (2006.01)
*G01R 33/56* (2006.01)
*A61B 5/00* (2006.01)
*G01R 33/565* (2006.01)

(52) U.S. Cl.
CPC ............ *A61N 5/1071* (2013.01); *A61B 5/055* (2013.01); *A61B 5/4836* (2013.01); *A61N 5/1039* (2013.01); *G01R 33/5608* (2013.01); *A61N 2005/1055* (2013.01); *A61N 2005/1074* (2013.01); *G01R 33/56509* (2013.01)

(58) Field of Classification Search
CPC ............................................. A61N 2005/1055
See application file for complete search history.

(56) References Cited

U.S. PATENT DOCUMENTS

| 7,708,682 | B2* | 5/2010 | Pekar | ..................... A61N 5/103 600/1 |
| 7,907,987 | B2* | 3/2011 | Dempsey | ............... A61B 5/055 600/411 |
| 8,190,233 | B2* | 5/2012 | Dempsey | ............... A61B 5/055 600/411 |

(Continued)

OTHER PUBLICATIONS

Ma et al. "Magnetic resonance fingerprinting", Nature 495.7440, pp. 187-192 (2013).

(Continued)

*Primary Examiner* — Angela M Hoffa
(74) *Attorney, Agent, or Firm* — Schiff Hardin LLP

(57) ABSTRACT

In a method and magnetic resonance (MR) apparatus for monitoring a radiation therapy of a patient, first MR image data are acquired with a quantitative magnetic resonance method before an irradiation of a target area of the patient, and second MR image data are acquired with the quantitative magnetic resonance method after the irradiation of the target area of the patient. The first MR image data and the second MR image data are compared, and output information is generated on the basis of a result of the comparison.

9 Claims, 2 Drawing Sheets

(56) References Cited

U.S. PATENT DOCUMENTS

| | | | | |
|---|---|---|---|---|
| 8,723,518 B2* | 5/2014 | Seiberlich | ............ | G01R 33/543 324/307 |
| 8,874,189 B2* | 10/2014 | Warntjes | ................ | A61B 5/055 345/617 |
| 9,014,424 B2* | 4/2015 | Berlinger | ................ | G06T 7/251 348/14.01 |
| 9,097,781 B2* | 8/2015 | Griswold | ........... | G01R 33/5612 |
| 9,114,253 B2* | 8/2015 | Dempsey | ................ | A61B 5/055 |
| 9,572,999 B2* | 2/2017 | Dempsey | ................ | A61B 5/055 |
| 9,889,318 B2* | 2/2018 | Dempsey | ............. | A61N 5/1064 |
| 9,958,521 B2* | 5/2018 | Kaditz | ................... | G01R 33/48 |
| 10,124,190 B2* | 11/2018 | Ojha | ...................... | A61B 5/055 |
| 10,180,476 B2* | 1/2019 | Cohen | ................ | G01R 33/4828 |
| 2005/0197564 A1* | 9/2005 | Dempsey | ................ | A61B 5/055 600/411 |
| 2006/0058637 A1 | 3/2006 | Sommer | | |
| 2007/0167748 A1 | 7/2007 | Rietzel | | |
| 2010/0113911 A1* | 5/2010 | Dempsey | ................ | A61B 5/055 600/411 |
| 2012/0022363 A1* | 1/2012 | Dempsey | ................ | A61B 5/055 600/411 |
| 2012/0235678 A1 | 9/2012 | Seiberlich et al. | | |
| 2013/0060128 A1* | 3/2013 | Stancanello | ......... | A61N 5/1039 600/411 |
| 2013/0072745 A1* | 3/2013 | Berlinger | ............. | A61N 5/1049 600/1 |
| 2013/0245425 A1* | 9/2013 | Dempsey | ............... | A61B 5/055 600/411 |
| 2013/0265047 A1 | 10/2013 | Griswold et al. | | |
| 2013/0267830 A1* | 10/2013 | Ojha | ...................... | A61B 5/055 600/411 |
| 2014/0121495 A1* | 5/2014 | Dempsey | ............... | A61N 5/1064 600/411 |
| 2016/0184609 A1* | 6/2016 | Dempsey | ............... | A61B 5/055 600/1 |
| 2017/0203126 A1* | 7/2017 | Dempsey | ............... | A61B 5/055 |
| 2018/0133511 A1* | 5/2018 | Dempsey | ............... | A61N 5/1064 |
| 2019/0022413 A1* | 1/2019 | Dempsey | ............... | A61N 5/1064 |
| 2019/0022414 A1* | 1/2019 | Dempsey | ............... | A61N 5/1064 |

OTHER PUBLICATIONS

Yankeelov "Integrating Imaging Data into Predictive Biomathematical and Biophysical Models of Cancer"; International Scholarly Research Network ISRN Biomathematics; vol. 2012; Article ID 287394; pp. 1-12; (2012).

Zahra et al: "Semiquantitative and quantitative dynamic contrast-enhanced magnetic resonance imaging measurements predict radiation response in cervix cancer"; Int. J. Radiation Oncology Biol. Phys.; vol. 74 No. 3; pp. 766-773; (2009).

Low "Gamma Dose Distribution Evaluation Tool", in: Journal of Physics, 2010, Conference Series 250, (2010).

* cited by examiner

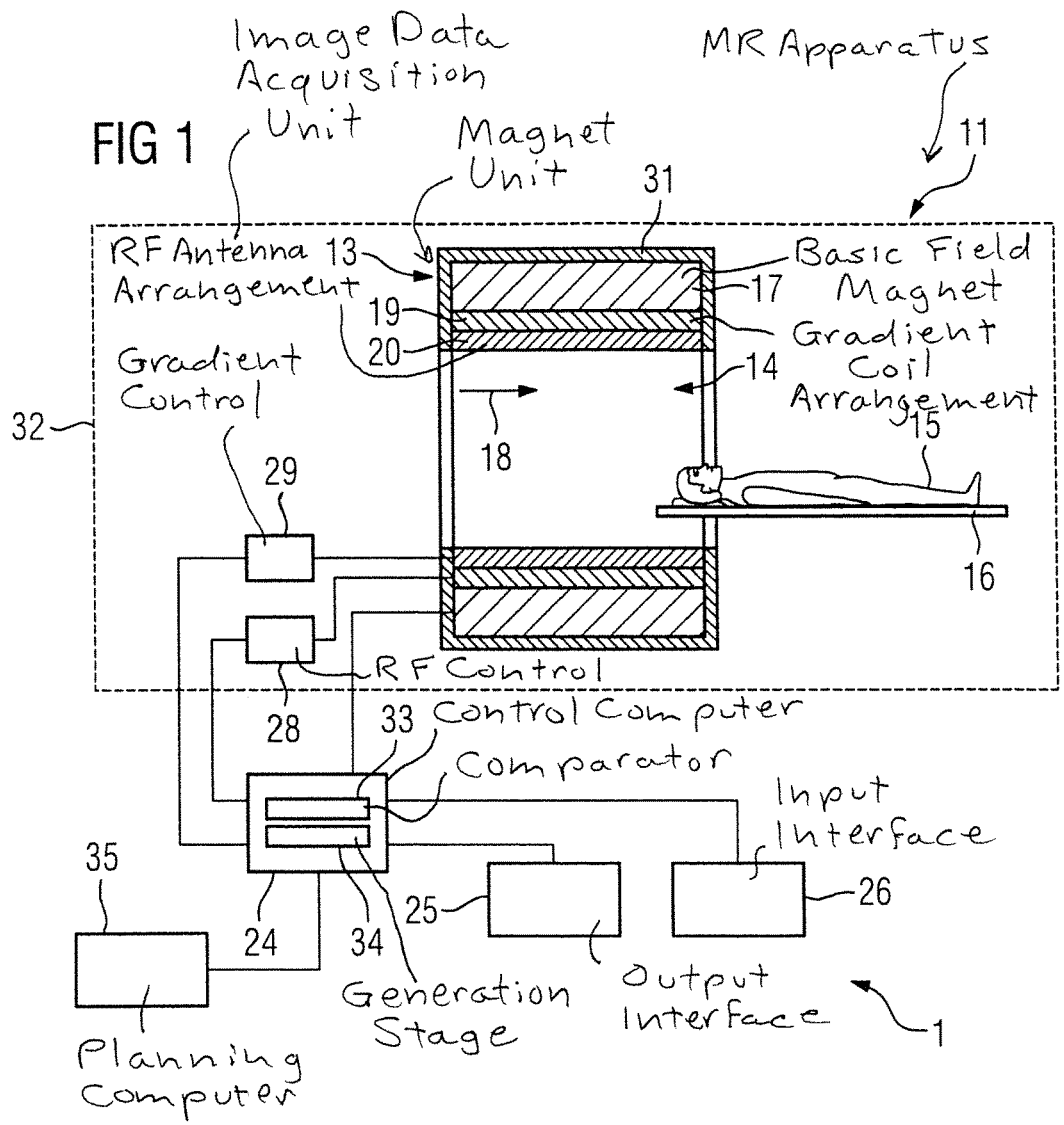
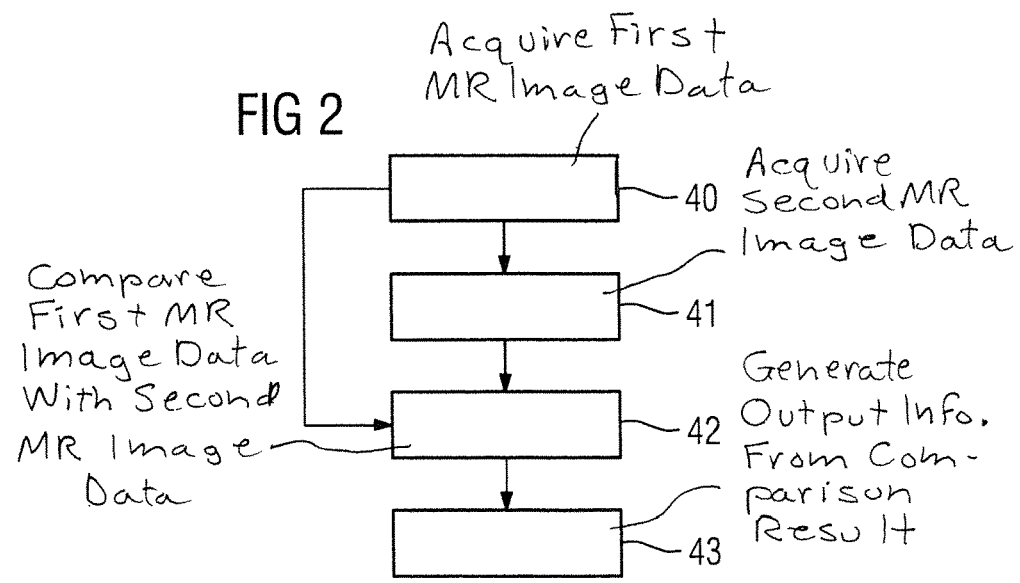

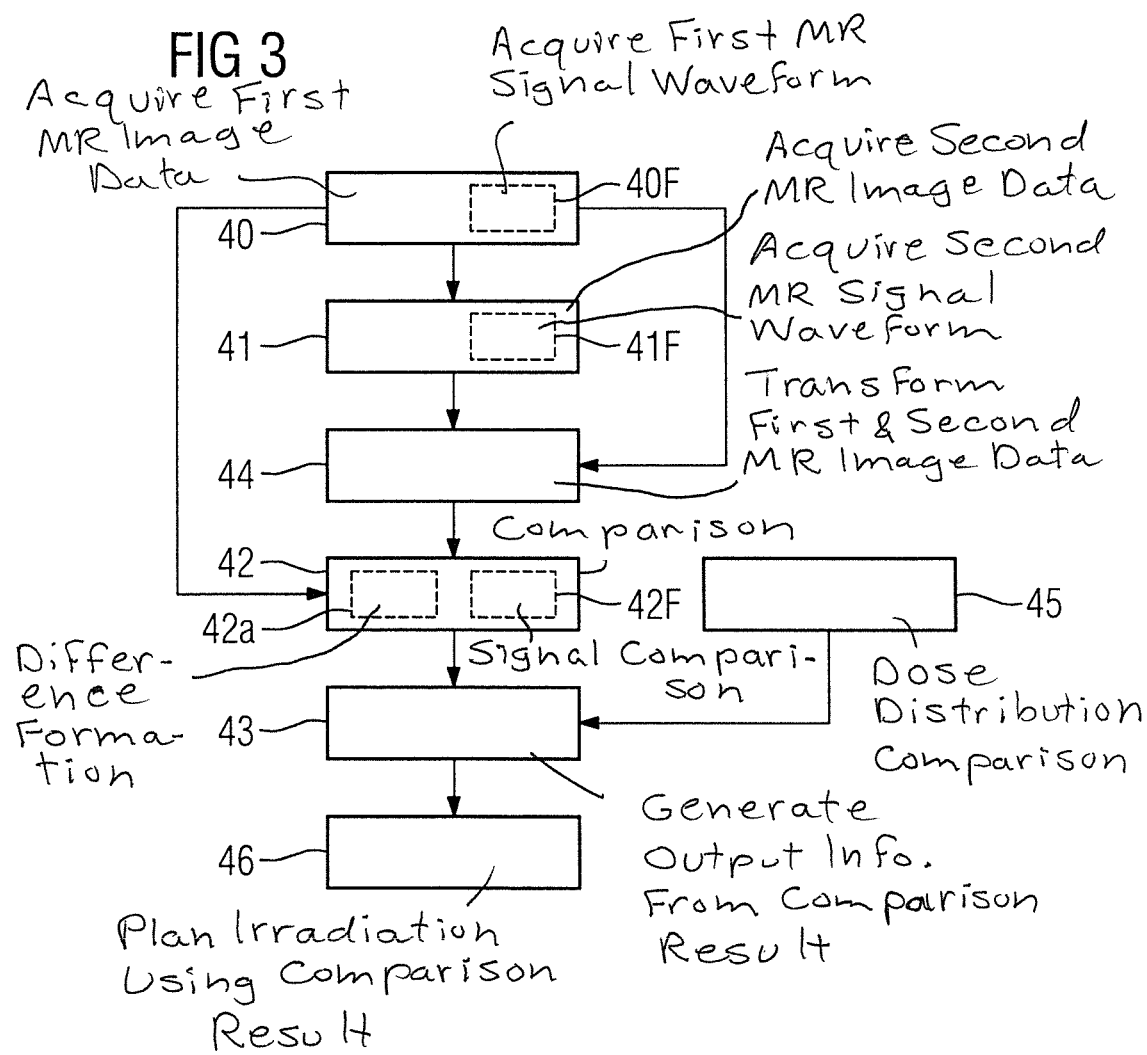

METHOD AND APPARATUS FOR MONITORING A RADIATION THERAPY OF A PATIENT

BACKGROUND OF THE INVENTION

Field of the Invention

The invention concerns a method for monitoring a radiation therapy of a patient, as well as a magnetic resonance apparatus and an apparatus for planning irradiation of a target area of a patient in accordance with such a method.

Description of the Prior Art

During the course of a radiation therapy target tissue, for example a tumor, of a patient is irradiated with ionizing radiation. External radiation therapy, wherein irradiation of the patient's body is done from outside the body, is a known procedure for this purpose. Likewise internal radiation therapy, also called brachytherapy, is known. In brachytherapy, radiation sources that embody radioactive substances are introduced into the patient's body in order to damage or to destroy the target tissue locally in the patient's body.

Planning and/or monitoring a radiation therapy of a patient by means of imaging are known. One of the methods used for planning and or monitoring a radiation therapy of the patient is magnetic resonance tomography, by the operation of a magnetic resonance apparatus.

In a magnetic resonance apparatus, also called a magnetic resonance tomography system, the body of a person to be examined is usually exposed, with the aid of a basic field magnet, to a relatively strong magnetic field, of 1.5 or 3 or 7 Tesla, for example. In addition gradient pulses are emitted by a gradient coil arrangement. Radio frequency (RF) pulses, particularly excitation pulses, are then emitted via a radio-frequency antenna arrangement by suitable antennas, which cause nuclear spins of specific atoms in the subject, that are excited resonantly by these RF pulses, to be flipped by a defined flip angle in relation to the magnetic field lines of the basic magnetic field. During the relaxation of these nuclear spins, radio-frequency signals, called magnetic resonance signals, are emitted, which are received by suitable radio frequency antennas and then further processed. From the raw data acquired with this manner, the desired image data can be reconstructed.

SUMMARY OF THE INVENTION

An object of the invention is to enable effective monitoring of a radiation therapy of a patient by MR data acquired with a magnetic resonance scanner.

This object is achieved in accordance with the invention by a method for monitoring a radiation therapy of a patient, which includes the following steps.

First magnetic resonance image data are acquired by execution of a quantitative magnetic resonance method before irradiation of a target area of the patient.

Second magnetic resonance image data are then acquired by execution of the quantitative magnetic resonance method after the irradiation of the target area of the patient.

The first magnetic resonance image data and the second magnetic resonance image data are then compared.

Output information is then generated on the basis of a result of the comparison.

The generated output information can be provided afterwards. The provision of the output information can be a display of the output information for a user on a display unit. As an alternative or in addition, the provision of the output information can be storage of the output information in a database. As an alternative or in addition the provision of the output information can be a transmission of the output information to a further computing system, wherein the further computing system can then further process the output information.

The target area preferably encompasses those target structures in the body of the patient that are to be irradiated by the radiation therapy. The target tissue is typically localized in the target area. The target area can be allocated a radiation dose in radiation planning. The target area is typically bordered by an area at risk, which includes tissue at risk. In the radiation planning, the area at risk can be allocated a maximum dose that may not be exceeded during the radiation therapy.

The quantitative magnetic resonance method that is employed for acquiring the magnetic resonance signals serves especially to determine at least one quantitative material parameter. In this case, a quantitative magnetic resonance method advantageously makes possible a quantification of the material parameter, which may be independent of measurement conditions or of the type of the magnetic resonance scanner. Thus the quantification of the material parameter can be independent of parameter settings, adjustment measurements, coil intensities, software versions etc. On the basis of magnetic resonance signals acquired in a quantitative magnetic resonance method the material parameters can thus be reproducibly reconstructed. A quantitative magnetic resonance image reconstructed from a quantitative magnetic resonance method thus advantageously contains information about absolute physical variables. Thus a value of an image pixel of such a quantitative magnetic resonance image advantageously has a direct relationship with a physical measured value. The value of the image pixel can have a physical unit. The value of the image pixel of the quantitative magnetic resonance image in this case is advantageously independent of measurement parameters, adjustment settings, the type of magnetic resonance scanner, imaging coils, etc. employed during the recording of the magnetic resonance image data. Thus magnetic resonance images recorded by different quantitative magnetic resonance methods, possibly under different measurement conditions, can be compared directly with one another.

Material parameters can be quantified by the magnetic resonance signals acquired in the quantitative magnetic resonance method. The material parameters are preferably quantified in a spatially-resolved manner. In particular, a spatially-resolved distribution of the material parameters is quantified. The material parameters advantageously characterize a physical characteristic of the substance, for example of the tissue from which the magnetic resonance signals are acquired. The material parameters can quantify a reaction of the substance to a radio-frequency excitation. The first magnetic resonance image data and/or the second magnetic resonance image data can include the spatially-resolved distribution of the material parameters.

The selection of possible material parameters that can be quantified in a quantitative magnetic resonance method includes the following: T1 relaxation time, T2 relaxation time, a diffusion value (for example an apparent diffusion coefficient, ADC), a magnetization moment, a proton density, a resonant frequency, a concentration of a substance, a temperature, etc. Naturally further parameters that appear meaningful to those skilled in the art are also conceivable. From these material parameters, any combination can be determined in the quantitative magnetic resonance method. The material parameters in such cases can be determined directly by the quantitative magnetic resonance method. The material parameters can in such cases be pixel values of the magnetic resonance image data acquired by the quantitative magnetic resonance method. The quantitative magnetic resonance method thus makes possible a direct characterization of the material parameter.

The image information is based on magnetic resonance images obtained from non-quantitative, especially qualitative methods, for example magnetic resonance images with a T2 weighting, typically merely on a signal comparison within a magnetic resonance image. Such non-quantitative magnetic resonance images thus typically deliver only a qualitative contrast between different substances. The values of the image pixels of non-quantitative magnetic resonance images can differ from examination to examination even with the same choice of parameters. The signal intensities determined in non-quantitative methods typically do not directly form a physical value. Typically only with an evaluation of different signal intensities relative to one another of a non-quantitative magnetic resonance image can a statement about physical characteristics which underlie the signal intensities be made.

The first magnetic resonance image data and second magnetic resonance image data acquired by the quantitative magnetic resonance method can advantageously be compared with one another. The reason for this is that the absolute values of the material parameters determined in the quantitative magnetic resonance method can be compared easily and informatively with one another. In such cases it is even possible for the acquisition of the first magnetic resonance image data and of the second magnetic resonance image data to be carried out by different types of magnetic resonance scanner, for example from different manufacturers. A comparison of qualitative magnetic resonance image data is often difficult to make in such cases, because typically different contrasts exist between the qualitative magnetic resonance image data to be compared. This can even be the case when the same recording settings for the recording of the qualitative magnetic resonance image data are used. In this way, by quantitative magnetic resonance for acquiring the first magnetic resonance image data and the second magnetic resonance image data, a better comparability of the first magnetic resonance image data and second magnetic resonance image data is achieved than if qualitative magnetic resonance methods were used for acquiring the magnetic resonance image data.

The comparison of the first magnetic resonance image data and the second magnetic resonance image data can include a determination of deviations and/or correlations between the first magnetic resonance image data and the second magnetic resonance image data. Particularly in this case the same material parameters between the first magnetic resonance image data and second magnetic resonance image data are compared with one another. On the basis of the comparison of the first magnetic resonance image data and the second magnetic resonance image data, the influence of the irradiation of the target area on tissue mapped by the magnetic resonance image data can be established. In this case the first magnetic resonance image data and the second magnetic resonance image data preferably include the target area. In particular the target area is entirely mapped in the first magnetic resonance image data and/or the second magnetic resonance image data. The first magnetic resonance image data and the second magnetic resonance image data in this case have recording areas that overlap at least partly, especially entirely.

The deviations and/or correlations can then be a part of the generated output information. The output information can include, for example, processed magnetic resonance image data, wherein, in the processed magnetic resonance image data, a difference and/or a match between the first magnetic resonance image data and the second magnetic resonance image data is identified. The output information can also include abstracted information. For example, the output information can include numerical values that characterize the degree of a change and/or a match between the first magnetic resonance image data and the second magnetic resonance image data.

Overall, by the inventive method, it is possible in an especially advantageous manner to follow the irradiation and it is carried out. For example, a reaction of a tissue localized in the target area to the irradiation can be characterized especially simply on the basis of the output information. Even fine changes in the tissue can be determined by comparing the absolute physical material parameters established by the quantitative magnetic resonance method. This offers an advantage particularly when a number of irradiations of the patient are being carried out on a number of days. A number of items (sets) of second magnetic resonance image data can then be recorded on different days, which are compared with the first magnetic resonance image data. In this way, the development of the tissue localized in the target area can be followed over a number of irradiations. On the basis of the output information, further irradiations of the patient can then be determined, in an especially advantageous manner. This irradiation plan for the further irradiation can be determined, for example, taking into account information as to whether target tissue is responding to the irradiation. As an alternative or in addition, a decision can also be made on the basis of the output information about continuing or stopping the irradiation.

Overall an especially advantageous procedure is achieved by the invention for monitoring a radiation therapy. Simple checking of the irradiation is possible. If a number of items of second magnetic resonance image data are recorded at different points in time in an irradiation cycle, the progress of the irradiations can also be checked. The use of a quantitative magnetic resonance method for acquiring the magnetic resonance image data in such cases ensures an advantageous comparability of the magnetic resonance image data after and before the irradiation.

In an embodiment, the comparison of the first magnetic resonance image data with the second magnetic resonance image data includes a differentiation between the first magnetic resonance image data and the second magnetic resonance image data. A differential image can be computed, for example, by the pixel values of the first magnetic resonance image data being subtracted from the pixel values of the second magnetic resonance image data—or vice versa. Changes between the first magnetic resonance image data and the second magnetic resonance image data are then especially apparent in the differential image. A weighted differentiation is naturally also conceivable. In this way, the differentiation offers an especially simple and informative method for identifying differences and/or similarities between the first magnetic resonance image data and the second magnetic resonance image data. A reaction of the target tissue to the irradiation can thus be identified especially easily.

In another embodiment, a transformation of the first magnetic resonance image data and/or the second magnetic resonance image data is made before the comparison, such that compensation can be made for different support positions of the patient during the acquisition of the first magnetic resonance image data and the second magnetic resonance image data. A transformation of second magnetic resonance image data can be carried out such that the support position of the patient in the first magnetic resonance image data and the second magnetic resonance image data are adapted to one another. For this purpose, the first magnetic resonance image data and the second magnetic resonance image data can be brought into registration with each other. The transformation can be made by a rigid registration using a rotation matrix and a translation vector. This technique is most advantageous for a rigid body movement, for example of the head or brain of the patient. A non-rigid registration can also be carried out. Compensation for the changes in support positions of the patient can also include a correction or a change of a positioning of organs of the patient in the body of the patient. As an alternative or in addition, it is also conceivable for the resolution of the first magnetic resonance image data and the second magnetic resonance image data to be adapted to each other. For the registration of the first magnetic resonance image data and the second magnetic resonance image data, anatomical and/or artificial markers can also be used. The markers can be recognized by means of a magnetic resonance fingerprinting method described in the following section. Naturally other methods appearing meaningful to those skilled in the art to compensate for different support positions of the patient are conceivable. Compensating for the different support positions leads to a better comparability of the first magnetic resonance image data and the second magnetic resonance image data. The transformation of the first magnetic resonance image data and the second magnetic resonance image data can be carried out before the differentiation described above.

In another embodiment, the quantitative magnetic resonance method is a magnetic resonance fingerprinting method. A suitable magnetic resonance fingerprinting method is known, for example, from the publication Ma et al., "Magnetic Resonance Fingerprinting", Nature, 495, 187-192 (Mar. 14, 2013). In a magnetic resonance fingerprinting method typically a number of magnetic resonance raw images of an examination area of the patient are acquired, wherein different recording parameters are set for the acquisition of the various magnetic resonance raw images. The acquisition of the number of magnetic resonance raw images of the examination area typically includes, for each magnetic resonance raw image among the multiple magnetic resonance raw images, an acquisition of a number of spatially-resolved magnetic resonance signal values. These signal values lie in one image area of an examination area. The signal values do not occur in k space. The magnetic resonance raw images in this case are typically not intended to be provided on a display unit, for example. The recording parameters can be varied in a pseudo-randomized way in the acquisition of the number of magnetic resonance raw images. Possible recording parameters that are changed in the acquisition of the number of magnetic resonance raw images are, for example, the echo time, the configuration and/or number of radio frequency pulses, the configuration an embodiment and/or number of gradient pulses, a diffusion encoding, etc. The number of magnetic resonance raw images can be acquired in this case during a number of repetition times, wherein one magnetic resonance raw image of the number of magnetic resonance raw images can be acquired in each case during one repetition time of the number of repetition times. A spatially-dependent magnetic resonance signal waveform is then generated over the number of magnetic resonance raw images. The magnetic resonance signal waveform thus specifies a change of recorded magnetic resonance signal values over the duration of the acquisition of the magnetic resonance signal waveform. A time resolution of the magnetic resonance signal waveform in this case is formed by a distance in time between the acquisition of two magnetic resonance raw images of the number of magnetic resonance raw images. This magnetic resonance signal waveform is then typically compared with a number of database signal waveforms stored in a database in a signal comparison. Advantageously in each case a different database of at least one material parameter is assigned to the various database signal waveforms. The database signal waveform then represents in each case the signal waveform to be expected in the magnetic resonance fingerprinting method when a sample, of which the material characteristics correspond to those of the associated database value of the at least one material parameter, is examined. The database signal waveforms can be established, for example, in a calibration measurement and/or simulated. The magnetic resonance fingerprinting method then typically allows a database signal waveform of the number of database signal waveforms to be assigned to the generated magnetic resonance signal waveform on the basis of the result of the signal comparison. The database value of the at least one material parameter belonging to the assigned database signal waveform can then be set as a measurement value of the at least one material parameter. The magnetic resonance fingerprinting method thus makes possible an especially advantageous quantification of the material parameter. In particular, a number of material parameters can be determined simultaneously by means of a magnetic resonance fingerprinting method. Only the acquisition of one individual magnetic resonance signal waveform for a voxel of the examination area is necessary in order to determine a number of material parameters by means of the magnetic fingerprinting method for the voxel. The material parameters determined in the magnetic resonance fingerprinting method can then be stored spatially-resolved as first magnetic resonance image data or second magnetic resonance image data. The first magnetic resonance image data and/or the second magnetic resonance image data can also include a number of spatially-resolved maps of various material parameters. The magnetic resonance fingerprinting method represents an especially advantageous method of acquiring the quantitative first magnetic resonance image data and second magnetic resonance image data.

In a further embodiment, the acquisition of the first magnetic resonance image data includes the acquisition of a first magnetic resonance signal waveform by the magnetic resonance fingerprinting method, wherein the first magnetic resonance signal waveform is acquired from tissue of the patient that is located in the target area of the irradiation. Also in this embodiment, for the acquisition of the second magnetic resonance image data includes an acquisition of a second magnetic resonance signal waveform by means of the magnetic resonance fingerprinting method and for the comparison of the first magnetic resonance image data, and the second magnetic resonance image data includes a signal comparison of the second magnetic resonance signal waveform with the first magnetic resonance signal waveform. The first magnetic resonance signal waveform can be stored in a database and be loaded from the database for the signal comparison. The output information can then be generated on the basis of the result of the signal comparison. Since the first magnetic resonance signal waveform is acquired from a tissue of the patient that is located in the target area of the irradiation, the first magnetic resonance signal waveform is recorded from the target tissue intended for the irradiation. A change of the target tissue therefore can be determined especially easily on the basis of the signal comparison. In particular an explicit search can be made in the second magnetic resonance image data for the presence of the target tissue. Thus a success of the irradiation of the patient can be established especially quickly. For example, a parameter can also be computed that characterizes a proportion of the target tissue in the first magnetic resonance image data and the second magnetic resonance image data. This parameter can be computed on the basis of information as to how often the first magnetic resonance signal waveform was measured in the first magnetic resonance image data and the second magnetic resonance image data. In this way the magnetic resonance fingerprinting method makes possible a comparison of the first magnetic resonance image data and the second magnetic resonance image data tailored specifically to the target tissue. In a similar way, a change in tissue at risk, for example radiation-sensitive tissue, by the irradiation can also be determined. For this the first magnetic resonance signal waveform is advantageously acquired from tissue-at-risk of the patient, which is located in an area at risk from the irradiation.

In another embodiment, the signal comparison of the second magnetic resonance signal waveform with the first magnetic resonance signal waveform includes a computation of a correlation of the second magnetic resonance signal waveform with the first magnetic resonance signal waveform by a correlation analysis. The correlation analysis makes it possible to compute a correlation value that specifies a degree of correlation of the second magnetic resonance signal waveform with the first magnetic resonance signal waveform. The output information can then include a spatially-resolved distribution of the correlation value. It can thus be specified especially simply whether there is still target tissue to be found in the second magnetic resonance image data.

In another embodiment, the first magnetic resonance image data and the second magnetic resonance image data are acquired from one examination area of the patient, wherein the examination area is delimited by a parallel excitation such that it is adapted in its shape to the target area of the irradiation. The parallel excitation is preferably undertaken by a pTX method, which is well known to those skilled in the art. Thus acquisition of the first magnetic resonance image data and the second magnetic resonance image data that are optimally matched to the target area is possible. In this way an area at risk from the irradiation can also be mapped.

In another embodiment, a first dose distribution is established before the irradiation of the patient, and a second dose distribution is established after the irradiation of the patient, and the first and the second dose distributions are compared with one another. A dose distribution can be established, for example, by a Gamma distribution. A Gamma distribution is known, for example, from the publication by Daniel A. Low "Gamma Dose Distribution Evaluation Tool", Journal of Physics: Conference Series 250 (2010). The dose distributions can be established in addition to the quantitative magnetic resonance image data. The dose distributions can provide additional information, on the basis of which a change caused by the irradiation can be characterized. It is therefore sensible to generate the output information using the comparison of the first and second dose distribution. The use of dose distributions in this case is especially advantageous since it typically takes account automatically of resolution differences or positioning differences of the patient before and/or after the irradiation.

In another embodiment, the output information to be transferred to a planning computer, in which an irradiation plan is established for a further irradiation of the patient using the output information. The establishment of the irradiation plan for the further irradiation of the patient can include an adaptation of an original irradiation plan for the irradiation of the patient already undertaken. Through the adaptation of the further irradiation plan, a changed distribution of the target tissue in the target area caused by the radiation already undertaken can be taken into account. Anatomical changes of the patient which have occurred can also be taken into account. Thus the further irradiation can be adapted especially advantageously, using the output information, to the irradiation already undertaken. For example, it is possible for the further irradiation to be adapted to changing peripheral conditions in the course of the radiation therapy of the patient. The irradiation plan thus can be adapted in an optimum manner to the further peripheral conditions underlying the irradiation.

The invention also encompasses on a magnetic resonance apparatus having an image data acquisition unit (scanner) and a computer with a comparison stage (module) and a generation stage, wherein the magnetic resonance apparatus is configured to carry out the inventive method.

The magnetic resonance device is thus configured to execute the inventive method for monitoring a radiation therapy of a patient. The image data acquisition unit is operated for the acquisition of first magnetic resonance image data by a quantitative magnetic resonance method before an irradiation of a target area of the patient, and for the acquisition of second magnetic resonance image data by the quantitative magnetic resonance method after the irradiation of the target area of the patient. A comparator of the computer makes a comparison of the first magnetic resonance image data and the second magnetic resonance image data. The generation stage is configured to generate output information on the basis of a result of the comparison.

The magnetic resonance apparatus can further include an output interface, for example a display unit, which provides the output information.

In an embodiment of the magnetic resonance apparatus, the comparator configured to make the comparison of the first magnetic resonance image data and the second magnetic resonance image data as a differentiation between the first magnetic resonance image data and the second magnetic resonance image data.

In another embodiment of the magnetic resonance apparatus, the comparator is configured to make, before the comparison, a transformation of the first magnetic resonance image data and/or the second magnetic resonance image data, such that compensation is made for different support positions of the patient during the acquisition of the first magnetic resonance image data and the second magnetic resonance image data.

In another embodiment of the magnetic resonance apparatus, the image data acquisition unit (scanner) is operated such that the quantitative magnetic resonance method is a magnetic resonance fingerprinting method.

In another embodiment of the magnetic resonance apparatus, the image data acquisition unit and the comparator are configured so that the acquisition of the first magnetic resonance image data includes an acquisition of a first magnetic resonance signal waveform by the magnetic resonance fingerprinting method, with the first magnetic resonance signal waveform being acquired from tissue of the patient that is located in the target area of the irradiation. Also in this embodiment, the acquisition of the second magnetic resonance image data includes an acquisition of a second magnetic resonance signal waveform by the magnetic resonance fingerprinting method, and the comparison of the first magnetic resonance image data and the second magnetic resonance image data includes a signal comparison of the second magnetic resonance signal waveform with the first magnetic resonance signal waveform.

In another embodiment of the magnetic resonance apparatus, the comparator is configured so that the signal comparison of the second magnetic resonance signal waveform with the first magnetic resonance signal waveform includes a computation of a correlation of the second magnetic resonance signal waveform with the first magnetic resonance signal waveform by means of a correlation analysis.

In another embodiment of the magnetic resonance apparatus, the image data acquisition unit is operated so that the first magnetic resonance image data and the second magnetic resonance image data are acquired from one examination area of the patient, with the examination area being delimited by a parallel excitation such that is adapted in its shape to the target area of the irradiation.

In another embodiment of the magnetic resonance apparatus, the comparator is configured to receive a first dose distribution that is established before the irradiation of the patient, receive a second dose distribution that is established after the irradiation of the patient, and to compare the first and the second dose distribution with one another.

In another embodiment of the magnetic resonance apparatus, the generation stage is configured to cause the output information to be transferred to a planning computer, and the planning computer is configured to establish an irradiation plan for a further irradiation of the patient using the output information.

Furthermore, the invention encompassed an apparatus for planning an irradiation of a target area of a patient, with an inventive magnetic resonance device in accordance with one of the embodiments described above, a planning computer configured to establish a parameter setting for the irradiation of the target area, which is connected to the computer of the magnetic resonance apparatus such that it is possible to establish the parameter setting on the basis of output information transmitted from the computer to the planning computer.

The advantages of the inventive magnetic resonance apparatus essentially correspond to the advantages of the inventive method that have been described in detail above. Features, advantages or alternate forms of embodiment mentioned above are likewise applicable to the apparatus. The functional claims of the method are embodied by corresponding physical modules, especially by hardware modules.

BRIEF DESCRIPTION OF THE DRAWINGS

FIG. 1 shows an inventive apparatus with an inventive magnetic resonance apparatus in a schematic diagram.

FIG. 2 is a flowchart of a first embodiment of the inventive method.

FIG. 3 is a flowchart of a second embodiment of the inventive method.

DESCRIPTION OF THE PREFERRED EMBODIMENTS

FIG. 1 schematically illustrates an inventive apparatus 1 for planning an irradiation of a target area of a patient 15.

The apparatus includes an inventive magnetic resonance apparatus 11. The magnetic resonance apparatus 11 has a detector unit formed from a magnet unit 13 with a basic field magnet 17 for creating a strong and constant basic magnetic field 18. The magnetic resonance apparatus 11 also has a cylindrical patient receiving area 14 for receiving a patient 15, wherein the patient receiving area 14 is cylindrically enclosed in a circumferential direction by the magnet unit 13. The patient 15 can be moved by a patient support 16 of the magnetic resonance apparatus 11 into the patient receiving area 14. The patient support 16 has a bed for this purpose, which is disposed movably within the magnet unit 13. The magnet unit 13 is shielded outwardly by housing cladding 31.

The magnet unit 13 also has a gradient coil arrangement 19 for creating magnetic field gradients, which are used for spatial encoding during imaging. The gradient coil arrangement 19 is activated by a gradient control unit 28. Furthermore the magnet unit 13 has a radio-frequency (RF) antenna arrangement 20, which is formed in the exemplary embodiment as a body coil integrated at a fixed location into the magnet unit 13. A radio-frequency antenna control unit 29 operates the RF antenna arrangement 20 so as to cause nuclear spins in the patient 15 to be deflected from the polarization that occurs in the basic magnetic field 18 created by the main magnet 17. The radio-frequency antenna unit 20 is controlled by the radio-frequency antenna control unit 29 to radiate radio-frequency magnetic resonance sequences into an examination area that is essentially formed by the patient receiving area 14. The radio-frequency antenna unit 20 is further embodied for receiving magnetic resonance signals from the patient 15.

To control the basic field magnet 17, the gradient control unit 28 and the radio-frequency antenna control unit 29, the magnetic resonance apparatus 11 has a control computer 24. The control computer 24 controls the magnetic resonance apparatus 11 centrally, for example to execute a predetermined imaging gradient echo sequence. Control information such as imaging parameters, as well as the reconstructed magnetic resonance images, can be provided for a user via an output interface 25, in the present case a display monitor, of the magnetic resonance apparatus 11. The magnetic resonance apparatus 11 also has an input interface 26 via which information and/or parameters can be entered by a user during a measuring process. The control computer 24 can include the gradient control unit 28 and/or radio-frequency antenna control unit 29 and/or the output interface 25 and/or the input interface 26. In the case shown the control computer 24 has a comparator 33 and a generation module or stage 34.

The magnetic resonance apparatus 11 further has an image data acquisition unit (scanner) 32 formed by the magnet unit 13 together with the radio frequency antenna control unit 29 and the gradient control unit 28.

The magnetic resonance apparatus 11 is designed, together with the image data acquisition unit 32 and the control computer 24, for implementing the inventive method.

The magnetic resonance apparatus 11 shown can naturally include other components that magnetic resonance apparatuses normally have. The general functioning of a magnetic resonance apparatus 11 is known to those skilled in the art, so that a detailed description of the further components is not necessary herein.

The apparatus 1 further includes a planning computer 35. The planning computer 35 is configured to establish a parameter setting for the irradiation of the target area. For this purpose, the planning computer 35 is connected to the control computer 24 of the magnetic resonance apparatus 11, especially to the generation stage 34, such that it is possible to establish the parameter setting on the basis of output information transmitted by the control computer 24 to the planning computer 35.

FIG. 2 is a flowchart of a first embodiment of the inventive method for monitoring a radiation therapy of a patient.

In a first method step 40, the image data acquisition unit 32 acquires first magnetic resonance image data by execution of a quantitative magnetic resonance method, before an irradiation of a target area of the patient 15.

In a further method step 41, the image data acquisition unit 32 acquires second magnetic resonance image data by execution of the quantitative magnetic resonance method after the irradiation of the target area of the patient 15.

Quantitative material parameters, which represent physically measurable variables, are acquired in the quantitative magnetic resonance method. In this way, in a further method step 42, an especially advantageous comparison of the first magnetic resonance image data and the second magnetic resonance image data is possible by means of the comparator 33 of the control computer 24. One reason for the simple comparability of the first magnetic resonance image data and the second magnetic resonance image data is because the image content of the first magnetic resonance image data and the second magnetic resonance image data are independent of recording parameters.

In a further method step 43, the generation stage 34 of the control computer 24 generates output information based on a result of the comparison. The output information can be provided to a user on the display monitor of the output interface 25. As an alternative or in addition, the output information can be stored in a database of the magnetic resonance apparatus 11. It is also conceivable for the output information to be used for irradiation planning, as described in the exemplary embodiment presented in FIG. 3.

FIG. 3 is a flowchart of a second embodiment of the inventive method for monitoring a radiation therapy of a patient.

The description given below is essentially restricted to the differences from the exemplary embodiment in FIG. 2, wherein, as regards method steps that remain the same, the description of the exemplary embodiment in FIG. 2 applies. Method steps that essentially remain the same are given the same reference numbers.

The second embodiment of the inventive method shown in FIG. 3 includes the method steps 40, 41, 42, 43 of the first form of embodiment of the inventive method according to FIG. 2. The second embodiment of the inventive method shown in FIG. 3 contains additional method steps and substeps. An alternate method sequence to that shown in FIG. 3 is also conceivable, which has only some of the additional method steps and/or substeps shown in FIG. 2. Naturally an alternate method sequence to that shown in FIG. 3 can also have additional method steps and/or substeps.

Before the comparison of the first magnetic resonance image data and the second magnetic resonance image data, a transformation of the first magnetic resonance image data and/or of the second magnetic resonance image data is carried out in a further method step 44 by the comparator 33, such that compensation is made for different support positions of the patient 15 during the acquisition of the first magnetic resonance image data and the second magnetic resonance image data. In the exemplary embodiment shown in FIG. 3 the second magnetic resonance image data are transformed and adapted to the first magnetic resonance image data. This can naturally also be done in the reverse direction.

The comparison of the first magnetic resonance image data and the second magnetic resonance image data can then include, in a substep 42a of the further method step 42, formation of a difference between the first magnetic resonance image data and the second magnetic resonance image data. The adaptation of the second magnetic resonance image data to the first magnetic resonance image data by the transformation enables the difference to be performed especially simply, such as by subtraction of the pixel values.

The quantitative magnetic resonance method for acquisition of the first magnetic resonance image data and second magnetic resonance image data employed in the first method step 40 and in the further method step 41, in the case shown in FIG. 3, is a magnetic resonance fingerprinting method. A magnetic resonance fingerprinting method typically includes recording of magnetic resonance signal waveforms, with a recording scheme with pseudo-randomized variable recording being used.

Thus the acquisition of the first magnetic resonance image data includes an acquisition of a first magnetic resonance signal waveform by the magnetic resonance fingerprinting method in a substep 40F of the first method step 40. The first magnetic resonance signal waveform is acquired in this case from a tissue of the patient 15 which is located in the target area of the irradiation. Thus the first magnetic resonance signal waveform represents a reference signal waveform, which characterizes a reaction of the target tissue to the recording scheme applied during the magnetic resonance fingerprinting method. The target tissue in such cases may include tumor tissue.

The acquisition of the second magnetic resonance image data includes an acquisition of a second magnetic resonance signal waveform by means of the magnetic resonance fingerprinting method in a substep 41F of the further method steps 41. The same recording scheme is employed as in substep 40F.

The comparison of the first magnetic resonance image data and the second magnetic resonance image data includes a signal comparison of the second magnetic resonance signal waveform with the first magnetic resonance signal waveform. This signal comparison is performed in substep 42F of the further method step 42. In the present exemplary embodiment, the signal comparison of the second magnetic resonance signal waveform with the first magnetic resonance signal waveform includes a computation of a correlation between the second magnetic resonance signal waveform and the first magnetic resonance signal waveform by means of a correlation analysis. This enables establishment of whether the second magnetic resonance signal waveform recorded after the irradiation is similar to the first magnetic resonance signal waveform recorded before the irradiation. This enables a change in the target tissue intended for irradiation to be characterized especially advantageously. In such cases, a number of second magnetic resonance signal waveforms are recorded at different spatial localizations. In such cases an explicit search can be made especially for the presence of the first magnetic resonance signal waveform in the number of second magnetic resonance signal waveforms. In this way, a spatial distribution of the tumor tissue after the irradiation can be determined.

In a further method step 46 the output information is transferred to a planning computer 35, in which an irradiation plan is then established for a further irradiation of the patient using the output information. For this purpose, the planning computer 35 is connected to the control computer 24 of the magnetic resonance apparatus 11, especially to the generation stage 34, so that the parameter setting can be established on the basis of output information transmitted by the control computer 24 to the planning computer 35. The planning computer 35 can also be a part of an irradiation apparatus, with which the irradiation of the patient is implemented.

The exemplary embodiment shown in FIG. 3 includes an optional method step 45, in which a first dose distribution before the irradiation of the patient is established, a second dose distribution after the irradiation of the patient is established and the first and the second dose distribution are compared with one another. Based on this comparison of the dose distributions, in further method step 43, the output information can be adapted especially advantageously. The optional method step 45 can also be performed with the aid of the first magnetic resonance image data and the second magnetic resonance image data. Thus the first dose distribution can be compared with the second dose distribution using a result of a spatial comparison of the first magnetic resonance image data with the second magnetic resonance image data.

It is also conceivable for an examination area of the patient 15, from which the first magnetic resonance image data and the second magnetic resonance image data is acquired in the method steps 40, 41, to be delimited by a parallel excitation such that the examination area adapts in its shape to the target area of the irradiation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for monitoring a radiation therapy administered to a patient, comprising:
   operating a magnetic resonance (MR) scanner with a quantitative MR fingerprinting method to acquire first MR image data before irradiating a target area of the patient with therapeutic radiation, the acquisition of the first MR image data including an acquisition of a first MR signal waveform associated with tissue of the patient in said target area;
   operating an irradiation apparatus to irradiate the target area of the patient with therapeutic radiation; operating the MR scanner with said quantitative MR fingerprinting method to acquire second MR image data after irradiating said target area of the patient with said therapeutic radiation, the acquisition of the second MR image data including an acquisition of a second MR signal waveform;
   in a processor, comparing said first MR image data and said second MR image data to obtain a comparison result by performing a signal comparison of said second MR signal waveform with said first MR signal waveform; and
   generating output information at an output of said processor dependent on said comparison result.

2. A method as claimed in claim 1, wherein the act of comparing said first MR image data and said second MR image data to obtain the comparison result comprises calculating a difference between said first MR signal waveform and said second MR signal waveform.

3. A method as claimed in claim 1 comprising, before comparing said first MR image data and said second MR image data, transforming at least one of said first MR image data and second MR image data to compensate for respectively different support positions of the patient during acquisition of said first MR image data and acquisition of said second MR image data.

4. A method as claimed in claim 1, wherein the act of comparing said second MR signal waveform with said first MR signal waveform comprises computing a correlation between said second MR signal waveform and said first MR signal waveform with a correlation analysis in said processor.

5. A method as claimed in claim 1 comprising acquiring said first MR image data and said second MR image data from a same examination area of the patient, said examination area being delimited by parallel excitation of nuclear spins therein so as to be adapted in shape to said target area.

6. A method as claimed in claim 1 comprising:
   in said processor, calculating a first dose distribution of said therapeutic radiation before said irradiation of the patient;
   calculating a second dose distribution of said therapeutic radiation after irradiation of the patient; and
   comparing said first and second dose distributions with each other,
   wherein the output information is generated at an output of said processor further based upon said comparison result of said first and second dose distributions.

7. A method as claimed in claim 1 comprising transferring said output information to a planning computer and, in said planning computer, establishing an irradiation plan for a further irradiation of a target area of the patient with therapeutic radiation using said output information.

8. A magnetic resonance (MR) apparatus comprising:
   an irradiation apparatus configured to irradiate a target area of a patient with therapeutic radiation;
   an MR scanner;
   a control computer configured to operate said MR scanner with a quantitative MR fingerprinting method to acquire first MR image data before irradiating the target area of the patient with therapeutic radiation, the acquisition of the first MR image data including an acquisition of a first MR signal waveform associated with tissue of the patient in said target area;
   said control computer being configured to operate said MR scanner with said quantitative MR fingerprinting method to acquire second MR image data after irradiating said target area of the patient with said therapeutic radiation, the acquisition of the second MR image data including an acquisition of a second MR signal waveform;
   a processor configured to compare said first MR image data and said second MR image data to obtain a comparison result by performing a signal comparison of said second MR signal waveform with said first MR signal waveform; and
   said processor being configured to generate output information at an output of said processor dependent on said comparison result.

9. An apparatus for planning irradiation of a target area of a patient with therapeutic radiation, comprising:
   an irradiation apparatus configured to irradiate a target area of a patient with therapeutic radiation;
   a magnetic resonance (MR) scanner;
   control computer configured to operate said magnetic resonance (MR) scanner with a quantitative MR fingerprinting method to acquire first MR image data before irradiating the target area of the patient with therapeutic radiation, the acquisition of the first MR image data including an acquisition of a first MR signal waveform associated with tissue of the patient in said target area;

said control computer configured to operate said MR scanner with said quantitative MR fingerprinting method to acquire second MR image data after irradiating said target area of the patient with said therapeutic radiation, the acquisition of the second MR image data including an acquisition of a second MR signal waveform;

a processor configured to compare said first MR image data and said second MR image data to obtain a comparison result by performing a signal comparison of said second MR signal waveform with said first MR signal waveform;

said processor being configured to generate output information at an output of said processor dependent on said comparison result; and a planning computer in communication with said processor, said planning computer provided with said output information and configured to establish a parameter setting for further irradiation of a target area of the patient with therapeutic radiation based on said output information.

* * * * *